United States Patent
Yueh (12)

(10) Patent No.: US 6,485,454 B1
(45) Date of Patent: Nov. 26, 2002

(54) AUTOMATIC INFUSION SET FOR CONTINUOUSLY INFUSING LIQUID MEDICINE OF DOUBLE BOTTLES

(75) Inventor: Sheng-Chi Yueh, 5 Fl., No. 7, Alley 65, Lane 71, Jiang-nan St., Taipei (TW)

(73) Assignees: Edward Yang, Taipei (TW); Sheng-Chi Yueh, Taipei (TW)

(*) Notice: Subject to any disclaimer, the term of this patent is extended or adjusted under 35 U.S.C. 154(b) by 87 days.

(21) Appl. No.: 09/689,879

(22) Filed: Oct. 13, 2000

(51) Int. Cl.$^7$ ............................................. A61M 5/14
(52) U.S. Cl. ........................................ 604/80; 604/31
(58) Field of Search ..................... 604/80, 151, 183, 604/254, 83, 67, 31, 81, 65

(56) References Cited

U.S. PATENT DOCUMENTS

| | | | |
|---|---|---|---|
| 4,316,460 A | * 2/1982 | Genese et al. | 604/31 |
| 4,838,856 A | * 6/1989 | Mulreany et al. | 604/65 |
| 4,941,875 A | * 7/1990 | Brennan | 604/81 |
| 5,059,173 A | * 10/1991 | Sacco | 604/80 |
| 5,127,904 A | * 7/1992 | Loo et al. | 604/83 |
| 5,152,746 A | * 10/1992 | Atkinson et al. | 604/31 |
| 5,242,392 A | * 9/1993 | Vaughn | 604/80 |
| 5,464,392 A | * 11/1995 | Epstein et al. | 604/67 |
| 5,593,385 A | * 1/1997 | Harrison et al. | 604/83 |
| 5,722,961 A | * 3/1998 | Fan | 604/254 |
| 5,911,708 A | * 6/1999 | Teirstein | 604/183 |
| 5,968,014 A | * 10/1999 | Neftel et al. | 604/151 |

FOREIGN PATENT DOCUMENTS

| | | | |
|---|---|---|---|
| DE | 2713248 | * 8/1980 | A61M/5/14 |
| DE | 19826655 | * 12/1999 | A61M/005/168 |

* cited by examiner

Primary Examiner—Teresa Walberg
Assistant Examiner—Leonid Fastovsky
(74) Attorney, Agent, or Firm—Bacon & Thomas, PLLC (57) ABSTRACT

Automatic infusion set for continuously infusing liquid medicine of double bottles, including a hollow circular barrel and a float-type sealing valve disposed in the circular barrel. The sealing valve has an I-shaped cross-section for reducing contacting area with inner wall of the circular barrel and preventing the sealing valve from attaching to the inner wall. A rubber-made membrane is disposed on each of two end faces of the sealing valve. An A bottle infusion catheter is passed through the circumference of a lower section of the circular barrel near the cap member at bottom end of the circular barrel, whereby the liquid medicine in double bottles can be automatic continuously infused and it is unnecessary to replace the exhausted drop bottle to save time. Moreover, the air in the vacant drop bottle is prevented from entering the vessels of a patient to lead to thrombosis.

3 Claims, 8 Drawing Sheets

AUTOMATIC INFUSION SET FOR CONTINUOUSLY INFUSING LIQUID MEDICINE OF DOUBLE BOTTLES

BACKGROUND OF THE INVENTION

The present invention relates to an infusion set, and more particularly to an automatic infusion set for continuously infusing liquid medicine of double bottles.

Figure 1:
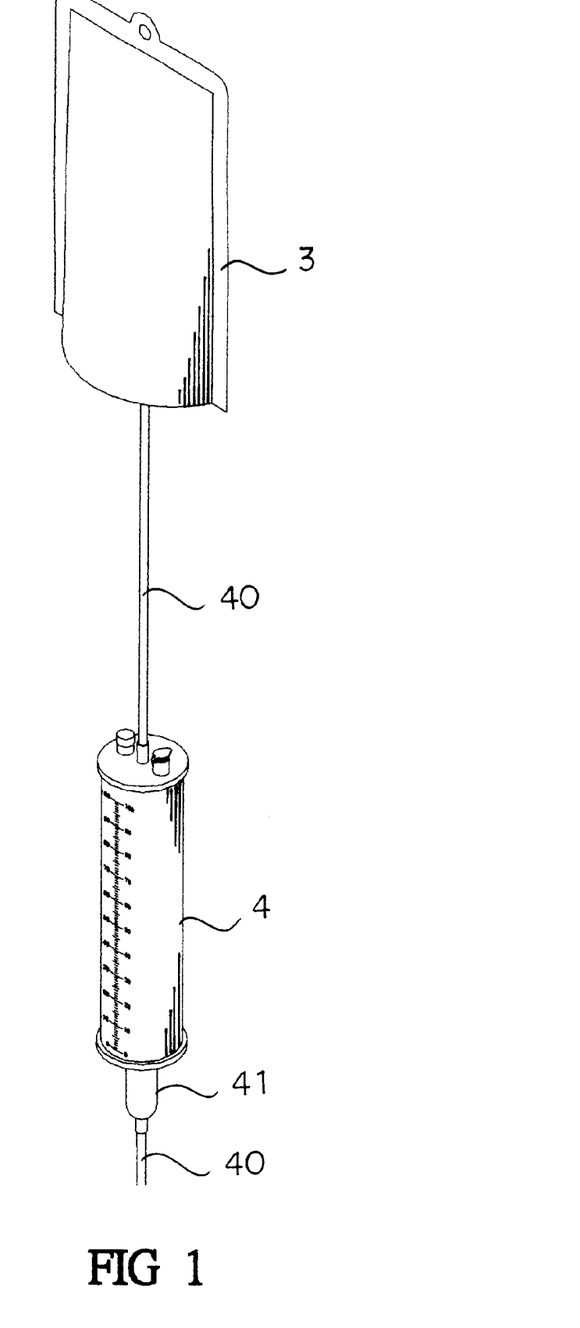
FIG. 1 is a perspective view of a conventional infusion barrel.

FIG. 1 shows a conventional drop bottle 3 and a cooperative infusion barrel 4 for intravenous injection. The amount of the infused liquid medicine must be controlled in accordance with the symptoms of a patient. In case that excessive amount or insufficient amount of liquid medicine is infused or there is no sealing valve, the air in the infusion barrel 4 may enter human body and lead to thrombosis. The infusion barrel 4 is connected with one drop bottle 3 via an upper plastic catheter 40. The drop bottle 3 is hung on a fixed position by means of an auxiliary cord. The lower end of the infusion barrel 4 is connected with a drop chamber 41 which is connected with a lower plastic catheter 40. The other end of the lower catheter 40 is fixed at a specific position of the patient.

The above structure has some shortcomings as follows:

1. The infusion barrel is generally connected with one single drop bottle. In the case that a patient needs to be continuously infused with multiple bottles of liquid medicine, after the liquid medicine in the first drop bottle is exhausted, it will be necessary to replace the drop bottle with a new one and again connect the catheter with the new drop bottle for further infusion. Such procedure is troublesome and time-consuming.

2. Such infusion barrel is equipped with any sealing valve. In case that the liquid medicine is totally infused and a medical guardian fails to notice this situation, the air in the vacant drop bottle will be filled into the vessels of the patient to lead to thrombosis.

SUMMARY OF THE INVENTION

It is therefore a primary object of the present invention to provide an automatic infusion set for continuously infusing liquid medicine of double bottles. The infusion set includes a hollow circular barrel and a float-type sealing valve disposed in the circular barrel. An A bottle infusion catheter is passed through the circumference of a lower section of the circular barrel near a cap member at bottom end of the circular barrel. The A bottle infusion catheter is connected to a second drop bottle, whereby the infusion can be connected with double drop bottles. After the liquid medicine in a first drop bottle is exhausted, the liquid medicine in the second drop bottle is automatically continuously infused. Therefore, it is unnecessary to replace the exhausted drop bottle and the time is saved.

It is a further object of the present invention to provide the above infusion set in which the float-type sealing valve disposed in the circular barrel is able to ensure safety in use of the infusion set.

It is still a further object of the present invention to provide the above infusion set in which the sealing valve has an I-shaped cross-section for reducing contacting area with inner wall of the circular barrel and preventing the sealing valve from attaching to the inner wall.

The present invention can be best understood through the following description and accompanying drawings wherein:

DETAILED DESCRIPTION OF THE PREFERRED EMBODIMENTS

Figure 2:
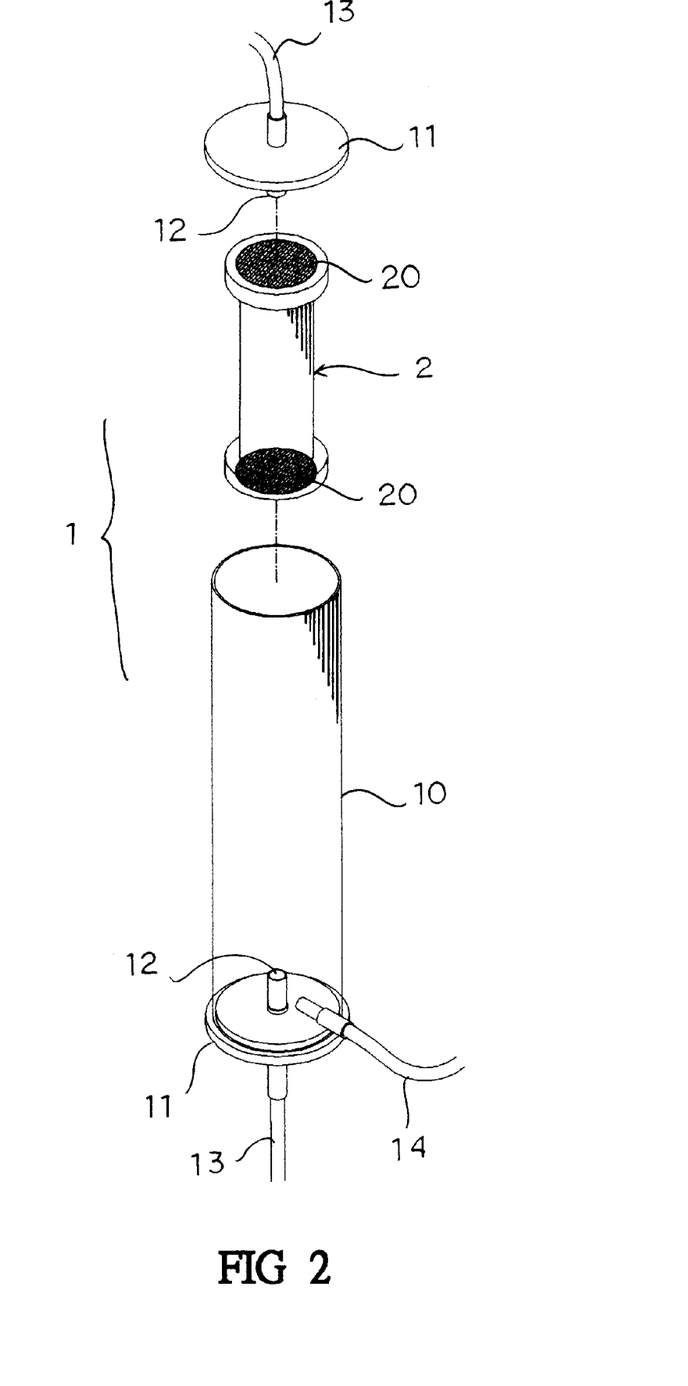
FIG. 2 is a perspective exploded view of a preferred embodiment of the present invention.
Figure 3:
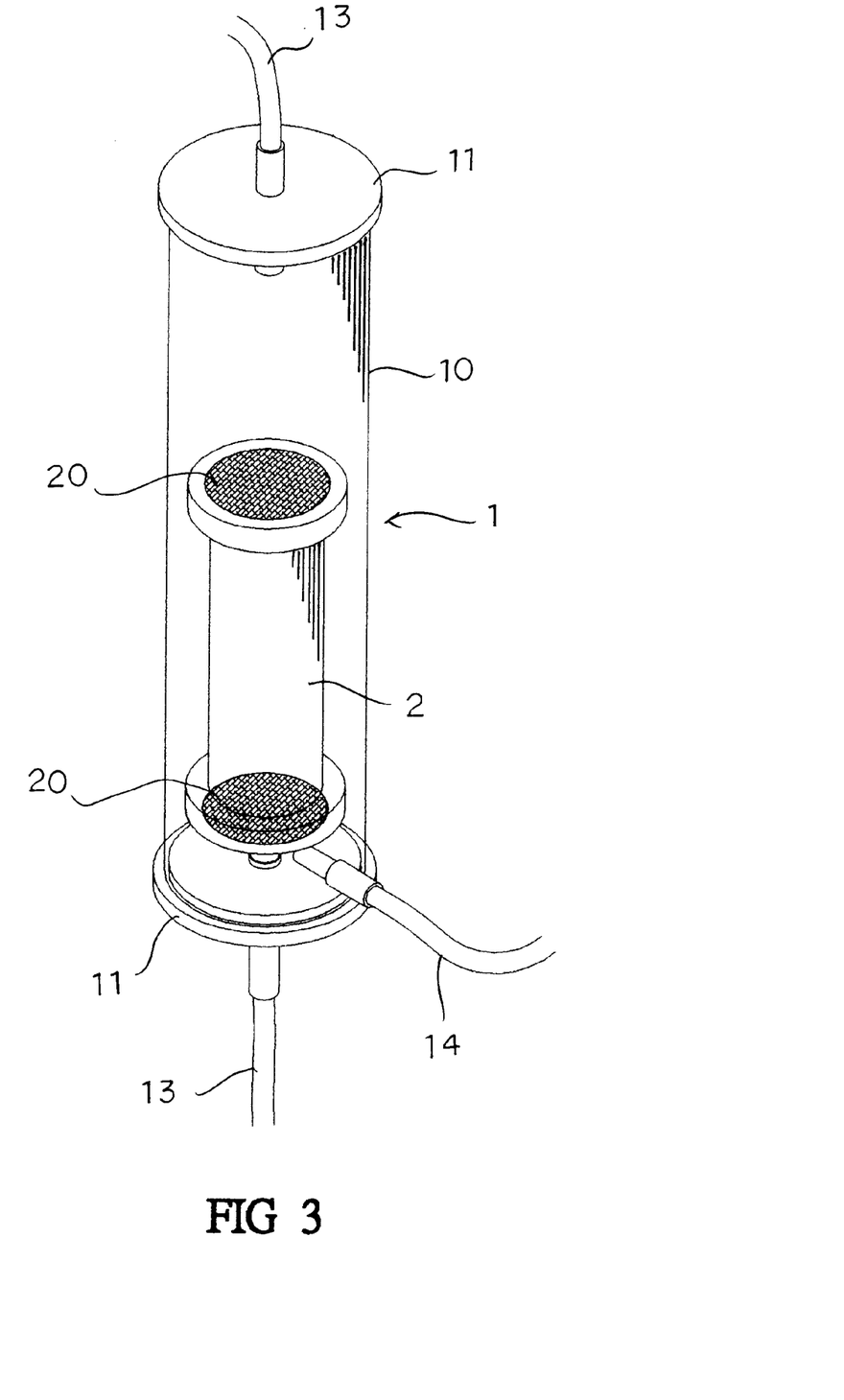
FIG. 3 is a perspective assembled view of the preferred embodiment of the present invention.

Please refer to FIGS. 2 and 3. The automatic infusion set 1 of the present invention includes a transparent circular barrel 10 and an I-shaped float-type sealing valve 2.

A cap member 11 is fitted with each end of the circular barrel 10. The cap member 11 is formed with a central infusion hole 12 for connecting with a B bottle infusion catheter 13. In addition, an A bottle infusion catheter 14 is passed through the circumference of a lower section of the circular barrel 10.

The float-type sealing valve 2 has a dimension slightly smaller than the diameter of the circular barrel 10 and has an I-shaped cross-section. A rubber-made membrane 20 is disposed on each of the upper and lower end faces of the sealing valve 2.

Figure 4:
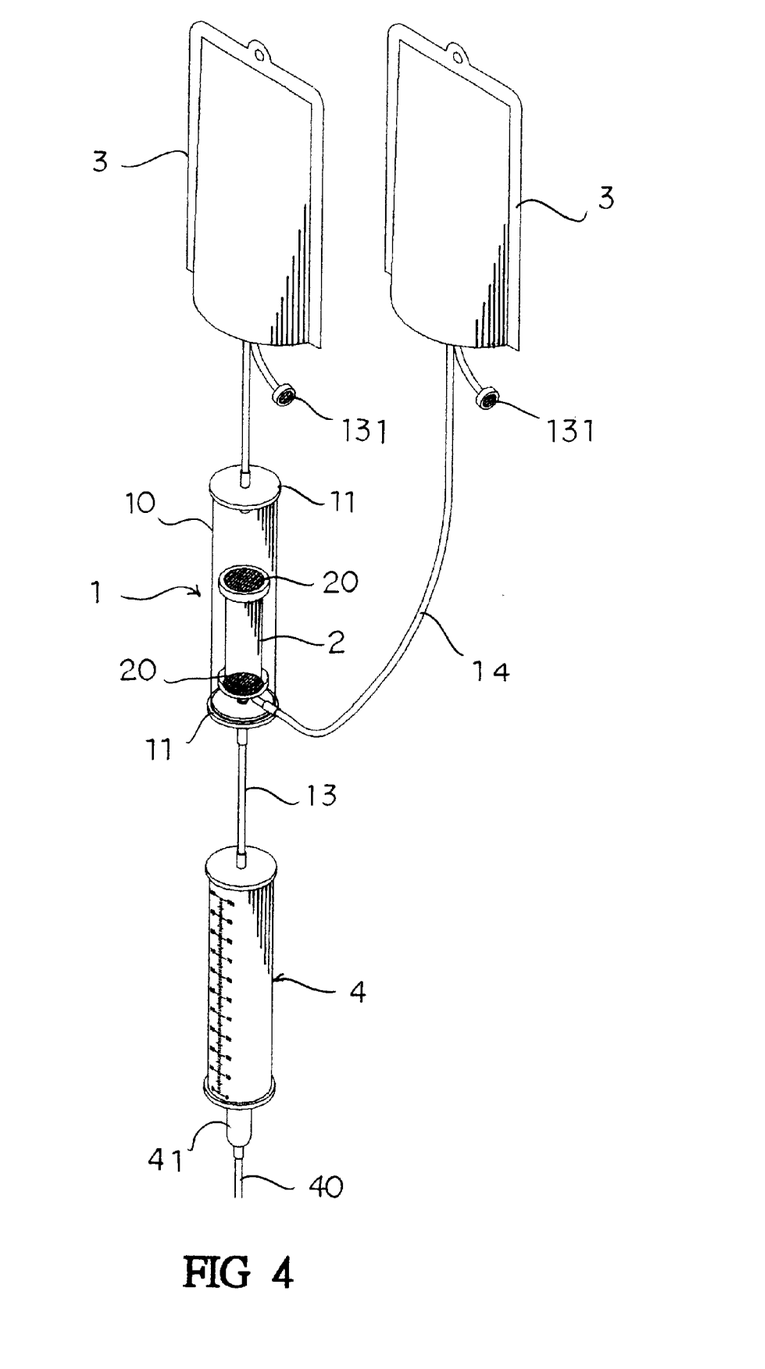
FIG. 4 shows the application of the preferred embodiment of the present invention of FIG. 3.
Figures 5A, 5B:
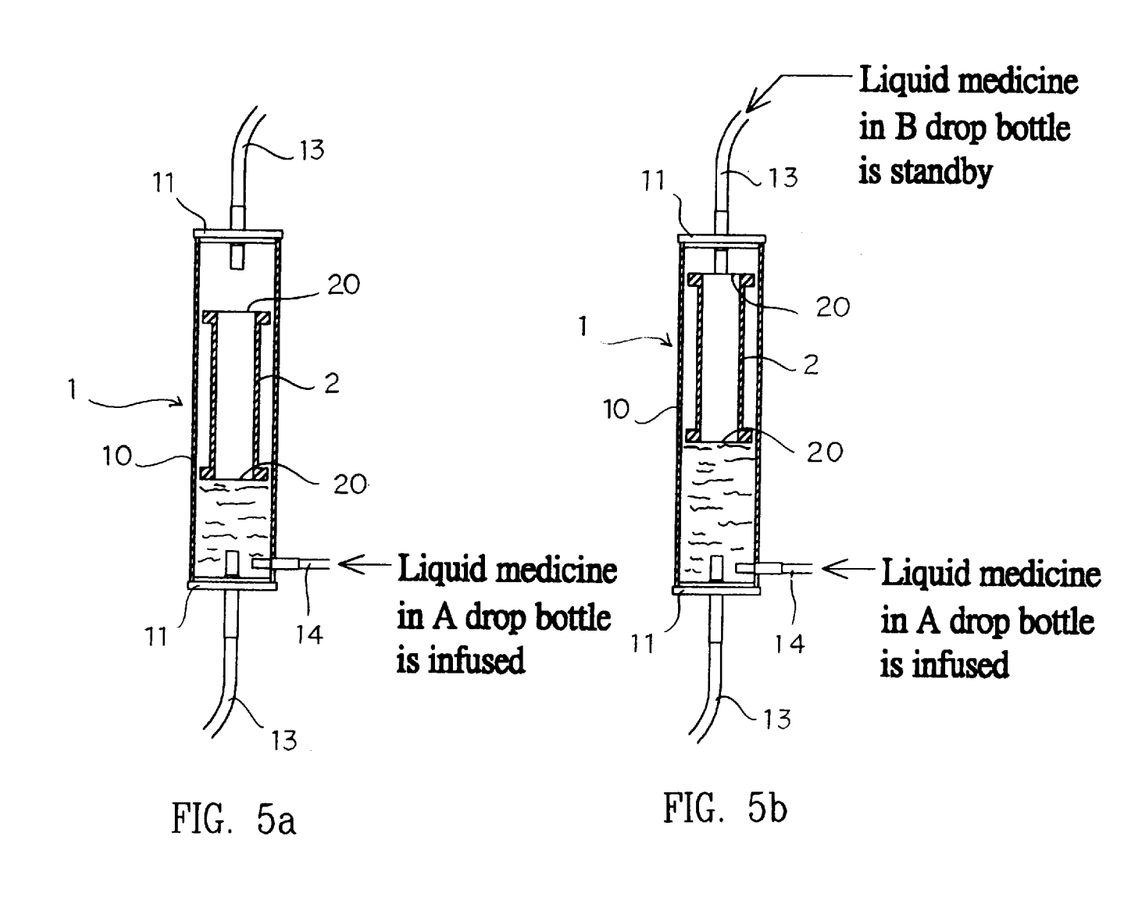
FIG. 5 is a sectional view showing the infusion operation of the preferred embodiment of the present invention in one state.
Figure 6A:
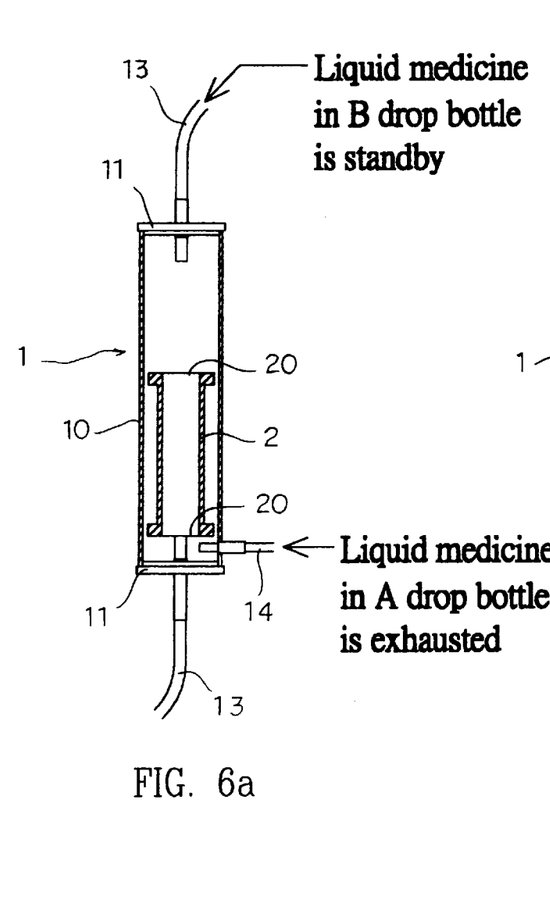
FIG. 6 is a sectional view showing the infusion operation of the preferred embodiment of the present invention in another state.
Figure 6B:
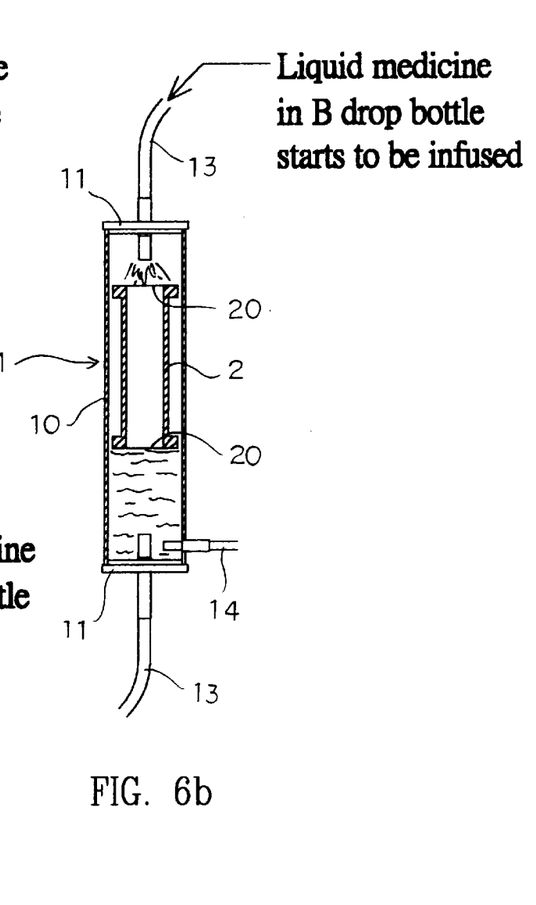

Referring to FIG. 4, in use, the infusion set 1 is installed between the B drop bottle 3 and the infusion barrel 4. The B bottle infusion catheters 13 at the centers of the cap members 11 are respectively connected to the B drop bottle 3 and the infusion barrel 4. The other end of the B bottle infusion catheter 13 is formed with a vent 131. Then the A bottle infusion catheter on the lower section of the infusion set 1 is connected with another A drop bottle 3. The other end of the A bottle infusion catheter 14 is also formed with a vent 131. Finally, the other end of the plastic catheter 40 of the conventional infusion barrel 4 is fixed at a specific portion of human body for injection. Accordingly, in infusion, the liquid medicine in the A drop bottle 3 is first filled into the infusion set 1. The liquid medicine then sequentially passes through the infusion barrel 4 and the infusion catheter 40 to be continuously infused into the human body. During the filling of the liquid medicine into the infusion set 1, the filling speed is faster than the infusion speed of the liquid medicine into the human body, so that the float-type sealing valve 2 in the infusion set 1 will gradually float up to the infusion hole 12 of the upper cap member 11. When the liquid medicine is about to be exhausted, the sealing valve 2 will sink onto the inner bottom face of the infusion set 1 as shown in FIG. 5. At this time, the liquid medicine in B drop bottle 3 starts to fill in. Similarly, during the filling procedure, the sealing valve 2 in the infusion set 1 will first float up and then sink as shown in FIG. 6. Therefore, it is unnecessary to troublesomely replace the exhausted drop bottle and the time is saved.

Figures 7A, 7B, 7C, 7D, 7E:
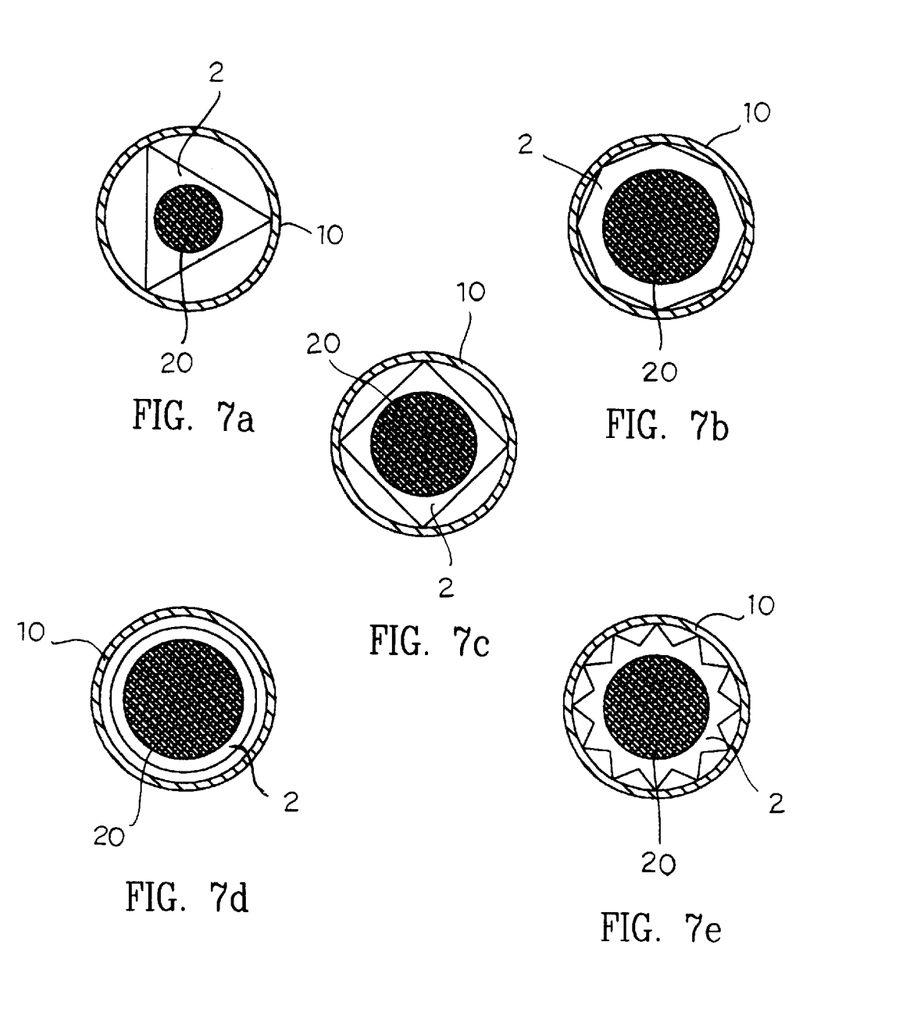
FIG. 7 shows various types of cross--sections of the float-type sealing valve of the present invention.

FIG. 7 shows the cross-sections of several different embodiments of the float-type sealing valve 2, in which the cross-section of the float-type sealing valve 2 can be circular, triangular, rectangular or polygonal. The membranes 20 are still disposed on the two end faces of the sealing valve 2. Accordingly, the sealing valve 2 is prevented from sticking with the inner wall of the circular barrel 10 due to excessively large contacting area, while still achieving the same function.

Figure 8A:
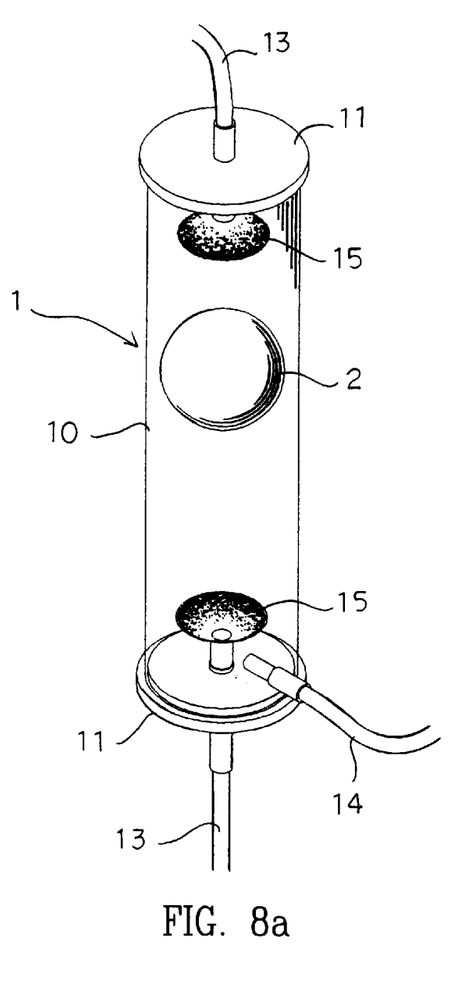
FIG. 8 is a perspective view of another preferred embodiment of the present invention.
Figure 8B:
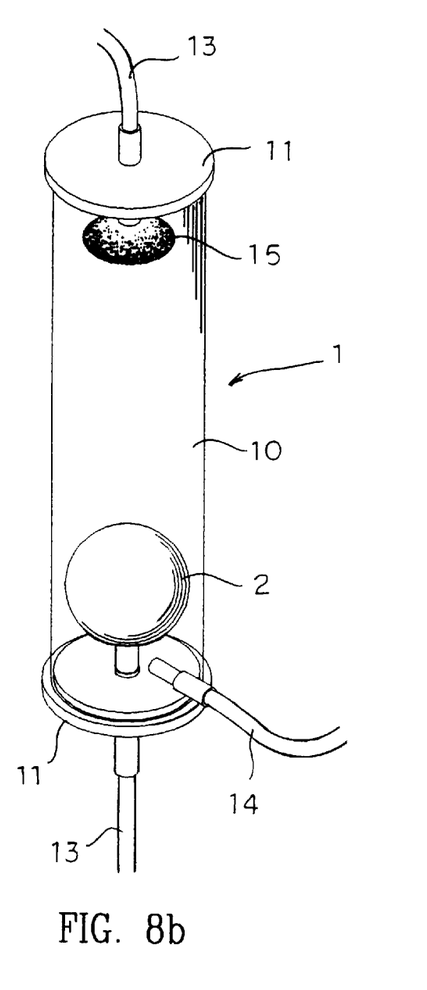

Referring to FIG. 8, according to another embodiment of the present invention, the inner face of the cap member 11 at each end of the circular barrel 10 can be formed with a bowl-like catching section 15 opposite to the other. Correspondingly, the sealing valve 2 is formed as a ball member cooperating with the catching section 15. This structure can achieve the same function.

The above embodiments are only used to illustrate the present invention, not intended to limit the scope thereof. Many modifications of the above embodiments can be made without departing from the spirit of the present invention.

What is claimed is:

1. Automatic infusion set for continuously infusing liquid medicine of double bottles, comprising:

a hollow circular barrel, a cap member being fitted with each of two ends of the circular barrel, the cap member being formed with a central infusion hole connecting with a B bottle infusion catheter, an A bottle infusion catheter being passed through the circumference of a lower section of the circular barrel near the cap member at bottom end of the circular barrel; and a float-type sealing valve having an I-shaped cross-section for reducing contacting area with inner wall of the circular barrel and preventing the sealing valve from attaching to the inner wall, a rubber-made membrane being disposed on each of two end faces of the sealing valve.

2. Automatic infusion set for continuously infusing liquid medicine of double bottles as claimed in claim 1, wherein the float-type sealing valve has a dimension slightly smaller than the diameter of the circular barrel and has a triangular, rectangular or polygonal cross-section.

3. Automatic infusion set for continuously infusing liquid medicine of double bottles as claimed in claim 1, wherein inner face of the cap member at each end of the circular barrel is formed with a bowl-like catching section opposite to the other and the sealing valve is formed as a ball member cooperating with the catching section.

\* \* \* \* \*